United States Patent [19]

Spires

[11] 4,394,377

[45] Jul. 19, 1983

[54] RUMINANT ANIMAL PERFORMANCE BY CO-ADMINISTERING CHOLINE AND PROPIONATE ENCHANCERS

[75] Inventor: Howard R. Spires, Sunnyvale, Calif.

[73] Assignee: Syntex (U.S.A.) Inc., Palo Alto, Calif.

[21] Appl. No.: 289,001

[22] Filed: Jul. 31, 1981

[51] Int. Cl.[3] .................... A61K 37/00; A61K 31/35; A61K 31/14

[52] U.S. Cl. .................................... 424/177; 424/115; 424/117; 424/283; 424/329

[58] Field of Search .............. 424/329, 283, 115, 117, 424/177

[56] References Cited

U.S. PATENT DOCUMENTS

| | | | |
|---|---|---|---|
| 3,873,719 | 3/1975 | Lorz et al. | 424/329 |
| 4,141,907 | 2/1979 | Nakatsukasa | 424/283 |
| 4,221,724 | 9/1980 | Liu et al. | 424/283 |

*Primary Examiner*—Sam Rosen
*Attorney, Agent, or Firm*—James M. Kanagy; Tom M. Moran

[57] ABSTRACT

The availability of supplemental dietary choline to animals with a developed rumen is increased by co-administering choline or choline compounds with a propionate-enhancing antibiotic compound.

32 Claims, No Drawings

RUMINANT ANIMAL PERFORMANCE BY CO-ADMINISTERING CHOLINE AND PROPIONATE ENCHANCERS

BACKGROUND OF THE INVENTION

1. Field of the Invention

The present invention relates to improving ruminant animal performance by increasing the postruminal availability of supplemental dietary choline to such animals. More specifically it relates to a method for improving ruminant animal growth, feed conversion and carcass quality by increasing the availability of supplemental dietary choline to animals with a developed rumen. This is achieved by co-administering choline with a propionate-enhancing antibiotic compound.

2. Prior Art

While choline supplementation of nonruminant diets has proved very effective for enhancing animal performance and is now widely accepted in the animal husbandry industry, direct supplementation of ruminant diets with choline is not currently practiced. This is because there has not been a clear indication that dietary supplementation with choline or choline compounds of any kind would be efficacious. This position is based in large part on research into the disposition of dietary choline in the rumen, both in vivo and in vitro, which indicates choline is rapidly catabolized to trimethylamine, acetate, ethanol or ethylene glycol, none of which are biologically active substitutes for choline itself. See Neill, Alan R. et al, *Biochem. J.* (1978) 170, 529–535).

Some field studies indicate choline or choline salts alone improve one or more performance parameters in ruminant animals. See Dwyer, I. A., *Animal Nutrition and Health,* October, 1969 and Fromsee, T. S., and R. Oltjen, 1975, *J. Animal Sci.,* 41:416. However, beneficial responses were not observed in other studies. See Harris, R. R., H. F. Eates and J. E. Barrett, Jr., 1966, *J. Animal Sci.* 25:248 and Weis, M. B., D. N. Blumer and E. R. Barrick, 1964, *North Carolina Agr. Exp. Sta. Ans. Report* 139, A. . Series 10 22). Ruminant dietary supplementation with choline fatty acid complexes, for example, choline stearate, has been claimed, in U.S. Pat. No. 3,873,719, to improve weight gain and/or quality of meat in ruminates while maintaining or improving feed conversion. However, the supplementation of meat producing ruminant diets with choline in any form is not currently a common practice.

There is no known art which indicates propionate-enhancing antibiotics will enhance the availability of choline in ruminant diets. A review of the activity of the propionate-enhancing polyether ionophore nigericin indicates it decreases mitochondrial oxidation of choline. See: Antibiotics I: Mechanism of Action, Ed D. Gottlieb and P. D. Shaw, Springer-Verlag New York, Inc., 1967, pp. 613–616. Inhibition of rumen fluid amino acid degradation by various antimicrobials, including a propionate-enhancing polyether ionophores, is noted in Schelling, G. T., et al, *Fed. Proc.* 37:411 (abstr.) 1978 and Chalupa, W., W. Corbett and J. R. Brethour, J. Animal Sci., 51:70, 1980.

Several U.S. patents, for example, U.S. Pat. Nos. 4,100,171, 3,790,668 and 3,927,836, claiming propionate-enchancing compounds disclose the use of surfactants, including lecithin, for preparing suspensions of water-insoluble forms of these compounds. None of these several patents disclose or intimate that co-administration of such antibiotics with a diet-supplementing amount of choline or choline containing compounds will affect the availability of choline to ruminant animals.

SUMMARY OF THE INVENTION

This invention comprises a method for increasing the availability of supplemental dietary choline to animals with a developed rumen which comprises co-administering a diet-suplementing amount of choline or choline compounds with a propionate-enhancing amount of a propionate-enhancing antibiotic compound.

Another aspect of this invention is a composition for increasing the availability of supplemental dietary choline to animals with a developed rumen which composition comprises a diet-supplementing amount of choline or a choline compound and a propionate-enhancing amount of a propionate-enhancing compound alone or in admixture with a carrier or feed.

DESCRIPTION OF THE PREFERRED EMBODIMENT

This invention is useful in ruminants which have a developed rumen function. The digestive system of young ruminants, basically those still unweaned, functions like that of nonruminant animals since their pregastric fermentatin system has not developed. However, as young ruminants begin to eat solid feed the function of the rumen begins to develop as the microbial population of rumen begins to build up. After the animals have eaten solid feed for a time their rumen function reaches full development and continues to operate throughout the animals' lives.

This invention is functional in all the ruminants, that is, the animals which have multiple stomachs, one of which is the rumen. The economically important animals are cattle, sheep, and goats.

Maintaining the improving animal performance parameters in these economically important ruminant animals, especially meat producing ruminants, is of considerable importance. These parameters include: (1) feed utilization, (2) animal growth rates, and (3) carcass quality.

Typically, relative utilization of feed is expressed as the ratio of feed consumed per pound of weight gain. Thus it is desirable to have a low feed to weight gain ratio. In addition, maximizing growth rates is desirable to achieve a market size animal in as short a period as is possible. Another factor of great importance is the yield and quality grade of meat obtained from the slaughtered animals. It is desirable that the carcass comes within the standards of the highest yield and grades possible.

There are numerous means available for maximizing animal performance parameters such as manipulation of diet; administration of drugs to enhance growth, prevent disease or increase the efficiency of feed utilization; specialized housing arrangements; selective breeding programs and the like. Dietary manipulation, more precisely dietary supplementation, is the focus in this invention.

Animal performance is directly affected by an animal's nutritional intake. While energy needs, protein requirements and adequate fat intake are basic to growth and health and are usually available in the grains, fodder and grasses making up the large part of an animals diet, other additional nutrients essential for good health, maximizing growth rates and maintaining feed efficiency are required in small quantities. These materials are termed micro nutrients. Optimum levels of these nutrients may not always be present in the primary dietary feed stuffs due to depleted soil on which grains, etc. are grown, poor growing conditions or genetically determined nutritient profile limitations. As a result micro nutrients are now commonly added to nonruminant and ruminant feeds as needed to supplement deficiencies which may exist in the various grains, fodder and grasses making up the bulk of an animal's diet.

Micro nutrients are generally vitamins and minerals. This invention involves ruminant diet supplementation of a vitamin B complex compound, choline. While choline alone usually is not added to ruminant feeds because no salutory affect on animal performance has been seen, it has now been found that co-administering choline with a propionate-enhancing compound can affect the availability of supplemental dietary choline to ruminant animals in such a manner as to enhance animal performance.

While the propriety of classifying choline as a vitamin and a member of the B-group is questioned by some, it is a necessary accessory factor to the B vitamins. Choline plays an important role both as a structural component of tissues and in biological methylation reactions.

Choline is ($\beta$-hydroxyethyl)trimethylammonium hydroxide. Because it is completely dissociated, it is comparable to an alkali hydroxide base. Consequently it does not exist as a base at body pH but rather as a salt, the anion is that present in its immediate biological enviroment. The ($\beta$-hydroxyethyl)trimethylammonium hydroxide cation is the biologically important moiety. The cation is incorporated into phospholipids, such as lecithin, sphingomyelin and acetyl choline.

Besides its vital function as a precursor of acetyl choline, which is important in sequence of nerve-muscle stimulation, choline is an important contributor of methyl groups needed for synthesis of metabolites and perhaps some hormones. Equally important is the fact that exogenous choline is an amino acid sparing material because it can regenerate methionine lost in transmethylation reactions thus making this essential amino acid available for use in protein synthesis. Choline also is a lipotropic agent; it acts to prevent the deposition of excess fat in the liver. The lipotropic action is independent of choline's function as a reservoir of methyl groups.

Choline and choline compounds of all types have utility in the practice of this invention. Choline compounds include the full scope of acid salts, fatty acid complexes, lecithin and similiar phosphatide compounds and various inner salt compounds comprising, for example, choline and phosphoric acid which are not choline esters of phosphoric acid.

Choline is a colorless, viscous, hydroscopic, strongly alkaline liquid. It is very soluble in water and ethanol. Choline can be prepared synthetically from triethylamine and ethylene chlorohydrin and ethylene oxide according to the procedure set out in U.S. Pat. No. 2,774,759.

Choline forms salts with inorganic and organic acids to give crystalline material. Choline is usually used as one of the various acid salts because the crystalline materials are substantially easier to handle than is the viscous, hygroscopic base itself. Acid salts are, for example, choline ascorbate, choline bicarbonate, choline chloride, choline citrate, choline bitartrate, choline dihydrogencitrate, and choline gluconate, to name some of the salts most readily available commercially.

Acid salts are the preferred form of choline for the practice of this invention. The hydrochloride salt of choline, choline chloride, is the most commonly available acid salt form of choline. It is the most preferred choline compound for the practice of this invention.

The preparation of the several recited choline salts is breifly recited here, though all can be obtained from commercial manufacturers. Choline ascorbate can be prepared from choline and ascorbic acid in methanol according to the procedure set out in U.S. Pat. No. 2,823,166. Choline bicarbonate can be prepared by passing carbon dioxide through a solution of choline until the pH reaction mixture is 9.0 or lower. The mixture is then concentrated and treated with carbon dioxide to pH of 8.5–8.9. Choline bicarbonate is finally isolated by vacuum evaporation of the solution. The preparation of choline chloride can be found in U.S. Pat. No. 2,623,901. Choline and citric acid are combined according to the procedure set out in U.S. Pat. No. 2,774,759 to give choline citrate (tricholinecitrate). Choline dihydrogen citrate, (2-hydroxyethyl)trimethylammonium citrate, is prepared according to the scheme set out in U.S. Pat. No. 2,870,198. The preparation of choline gluconate, the D-gluconic acid salt of choline is given in U.S. Pat. No. 2,691,617.

While several choline acid salts are specifically recited here, it should be understood the scope to this invention is not to be limited by the recitation of these specific acid salt compounds. Any choline acid salts would have utility as a dietary supplement herein as long as it did not demonstrate any untoward or deleterious physiological effect on ruminant animals or on the function of the rumen itself.

Also having utility in this invention are choline fatty acid complexes (FAC) which comprise choline salts of various fatty acids. Such complexes are exemplified by the stearic acid/choline complexes disclosed in U.S. Pat. No. 3,873,719. These fatty acid complexes are made up of choline stearate alone or choline stearate in admixture with choline salts of other fatty acids having 14–22 carbon atoms. The preparation of these specific fatty acid complexes, including both choline stearate and choline stearate with one or more choline salts of fatty acids can be found in the above mentioned patent, which is incorporated herein by reference.

Additionally, there are a number of other choline containing compounds which can be used in the practice of this invention. One group of such compounds are the choline containing phospholipids, best exemplified by the phosphatide lecithin or phosphatidylcholine. These compounds comprise choline esters of phosphoric acid linked to mixtures of fatty acids by polyols. Lecithin, for example, is a mixture of the diglycerides of stearic, palmitic and oleic acids linked to the choline ester of phosphoric acid. Numerous lecithin related compounds such as, for example, lauroyldesoxylysolecithincholine (hydroxide, 3-hydroxypropyl hydrogen phosphate, inner salt, laurate, CAS No. 25800-40-2) have been prepared. A number of other compounds containing choline and phosphoric acid, but where choline is not the ester of phosphoric acid, are in the art. For example, choline, hydroxide, dihydrogen phosphate, inner salt ester with 1-monostearin, DL-, (CAS No. 17364-19-1). While it is possible to use these and similar materials, it is commercially more desirable and more convenient to employ choline salts.

Central to the practice of this invention is the use of certain antibiotics to reduce rumen microbial degradation of choline. Generically the antibiotics of interest can be characterized as propionate-enhancing compounds. The activity of these drugs was discovered as a result of research into rumen carbohydrate metabolism. Investigations into the efficiency of feed use in ruminants indicated that the mechanism of carbohydrate utilization in ruminants proceeded by rumen microbial degradation of carbohydrates to produce volatile fatty acids, particularly acetic, propionic and butyric acid. In the overall scheme, propionic acid is the most efficiently utilized end product or ruminal carbohydrate metabolism. Thus, the efficiency of carbohydrate utilization can be increased if the rumen microbial population can be made to shift its production of volatile fatty acids to produce less acetic and butyric acid and more propionic acid.

Research on this problem disclosed that certain antibiotics could, in fact, effect a shift in rumen volatile fatty acid production from acetate to propionate. Antibiotics having such activity are now commonly called propionate-enchacing or propionate-increasing compounds. They are widely used in the raising of meat producing animals with a developed rumen.

Propionate-enhancing activity is not limited to a particular class of compounds although some compound types are more active than others. For example, such diverse compounds as a hemiacetal of chloral, halogenated acyclic carboxcyclic acids, peptides, thiopeptides, polyhaloalkyl substituted aminoethanol derivatives, polyhaloalkoxy substituted benzene derivatives and the ionophoric group of antibiotics exemplified by polycyclic ether compounds, known as polyether ionophores, all demonstrate propionate-enhancing activity. While all these compounds demonstrate propionate-enhancing activity to a greater or lesser degree, the ionophore compounds, particularly the polyether ionophores, show the greatest degree of propionate-enhancing activity and as a result are the most widely used compounds in this area for improving the feed efficiency of ruminants.

It has now been found that antibiotics having such propionate-enhancing activity also decrease rumen microbial degradation of choline when choline or choline compounds and such drugs are administered together. Thus by co-administering these two materials it is possible to effectively and economically enhance ruminant animal performance by means of choline. It is expected that other antibiotics which have the same general structure and properties as described above will be useful in this invention.

While any propionate-enhancing antibiotic generally will be effective in the practice of this invention it is preferred to use one or more of the ionophoric antibiotics. Their one common denominator is that they are compounds which can be characterized biologically by their monovalent metal cation transporting properties. Pinkerton et al, *J. Mol. Biol.*, 49, 533–466 (1970) discussed the molecular structure of some of these ion transporting complexes and provides insight into the mechanism of their biological action.

This group of polycyclic ether antibiotics, also called polyether ionophores, comprise a chemically and structurally heterogenous group of compounds. Their one common characteristic is that they are able to complex with monovalent metal ions, such as sodium and potassium, and render such ions organic solvent soluble. These polycyclic ethers enfold a metal ion, forming a loop or ball around the ion with the oxygen function adjacent to the metal and the hydrocarbon backbone forming the exterior of the complex. This three dimensional arrangement, coupled with the fact there is no net charge on the complex, render the whole complex organic solvent soluble. The molecule is able to maintain its loop or ball configuration because of hydrogen bonding between the chemical moieties affixed to opposite ends of the molecule. Usually this involves an acid and an hydroxyl group.

Some such compounds comprise a chain of 5, 6 or more cyclic ether moieties with a carboxylic acid function at one end and one or more hydroxyl groups at the other. Others lumped into this class have only one or two such ring structures, or may have nitrogen containing rings. All have at least one acid function.

One preferred group of ionophores is that group of polyether compounds represented by such compounds as monensin, dianemycin, narasin, nigericin, laidlomycin and a number of other related compounds which are designated by various given names and research numbers. The salts and esters of such compounds are also known to exhibit propionate-enhancing activity and are to be included in this invention.

This group is the most widely investigated of the various polyether ionophores. These antibiotics are polyether, polyalcohol, monocarboxylic acids of molecular weight 700–1000. All are effective against gram-positive bacteria. They were first used for controlling coccidiosis in chickens.

The best known of these compounds is monensin, also identified as A-3823, which is described by Haney et al, U.S. Pat. No. 3,501,568. The substance known as monensin is actually a mixture of four factors, all of which are included in the term monensin. Monensin is produced by fermentation by an organism, *Streptomyces cinnamonensis,* which is on unrestricted deposit under the number ATCC 15413 at the American Type Culture Collection, 12301 Park Lane Drive, Rockville, MD 20852. Methods for preparing and isolating monensin can be found in the Haney patent and in numerous other references, such as, for example, Stark et al, *Antimicrob. Ag. Chemother.* (1977) 353. The structure of monensin was determined by Agtarap et al, *J. Am. Chem. Soc.* A9, 5737 (1967).

Monensin is marketed for use as a coccidiostat under the name Coban ® and for use as a propionate-enhancing drug in ruminants under the trademark Rumensin ® (Trademarks of the Elanco Products Co., Indianapolis, Ind.

The deshydroxymethyl derivative of monensin also exhibits propionate-enhancing activity. A method for preparing this compound is disclosed in U.S. Pat. No. 3,839,557.

Dianemycin is a fermentation product of an organism which is a strain of *Streptomyces hygroscopicus.* It is on unrestricted deposit under the identifying number NRRL 3444 at the Northern Utilization Research and Development Div., Agricultural Research Service, United States Department of Agriculture, 1815 North University Street, Peoria, Ill. 61604.

Gorman et al, U.S. Pat. No. 3,577,531 teaches the preparation, characteristics and description of dianemycin and refers to an early article about it by Lardy et al, *Arch. Biochem. Biophysics* 78, 587–97 (1958). Structural characterization of this compound was carried out by Steinrauf et al, *Biochemical. and Biophysical Research Communications* 45, 1279–87 (1971).

Narasin is a given name for an antibiotic complex also designated A-28086. This is made up of several structurally related factors designated A, B and D produced by submerged aerobic fermentation of *Streptomyces aureofaciens* NRRL 5758. The main component is the B component, or narasin B.

This complex is described in U.S. Pat. Nos. 4,035,481 and 4,038,384 to D. H. Berg, et al. Semi-structural formulas for factors B, C and D are given in these patents along with culture media compositions, fermentation conditions, isolation and separation techniques for all materials comprising this complex. Esters of A-28086 are also disclosed as having propionate-enchancing activity.

Nigericin has been known at various times as helexin C, antibiotic X464, antibiotic K178, polyetherin A, and azalomycin M. It has been structurally characterized by Steinrauf et al, *Biochemical. and Biophysical Research Communications* 33, 29 (1968). Nigericin was originally reported by Harnes, et al, *Antibiotics and Chemotherapy,* 1, 594–96 (1951). It has also been described in Gorman et al, U.S. Pat. No. 3,555,150.

The organism which produces nigericin, a strain of *Streptomyces violaceoniger,* is on unrestricted deposit as NRRL B 1356 at the Northern Utilization Research and Development Div., Agricultural Research Service, U.S. Department of Agriculture, 1815 North University Street, Peoria, Ill. 61604. Methods for preparation and isolation of this material can be found in the Gorman Patent and in U.S. Pat. No. 3,937,836.

Additionally the deshydroxymethyl form of nigericin can be used in the practice of this invention. The bacterial source and methods for producing nigericin can be found in U.S. Pat. No. 3,937,836 which also contains a method for producing the deshydroxymethyl form of this compound.

Another relative of the polyether ionophore monensin type antibiotics which increase propionate production in rumen flora are two compounds originally described by the numbers A28695A, and A28695B, and their physiologically acceptable salts. Antibiotic A28695A is now conventionally referred to as septamycin. Both compounds are produced along with other unspecified antibiotic substances by culturing the microrganism *Streptomyces albus* NRRL 383 in an aqueous nutrient culture medium. Under submerged aerobic fermentation conditions. The antibiotic factor A28695A is produced in greater abundance than is antibiotic A28695B. Culture medium compositions, pH conditions, times to harvest, isolation and separation techniques are all available in U.S. Pat. No. 3,856,940.

The structural characterization of A28695A, septamycin, was determined by C. Keller-Juslin as reported in the *J. Antibiotics,* Vol 28, No. 11, pp. 854–859 (1975). Fraction B was structurally characterized by D. Dorman, et al, in the *J. Antibiotics,* Vol 33, No. 2, pp. 252–255 (1980).

The polyether ionophore, salinomycin, is also of interest herein. The salinomycin producing organism is a streptomyces organism designated as the strain NO80614, isolated from a soil sample collected at Fuji City, Shizuoka, Prefecture, Japan. According to taxonomical studies this organism is identified with a strain of *Streptomyces albus* (Rossi-Doria) Waksman and Henrici. The type strain has been deposited in the Fermentation Research Institute, Chiba, Japan and American Type Culture Collection, Rockville, Md. and accessioned as FERM-P No. 419 and ATCC 21838, respectively. Detailed morphological, cultural and physiological characteristics of this strain are set out extensively in the *Journal of Antibiotics,* Vol. 27, No. 11, p. 814–821.

Laidlomycin, chemically related to monensin, is also of interest herein. Laidlomycin is obtained from culture filtrates of *Streptomyces eurocidicus var. asterocidicus* (Streptomyces S-822) as outlined by Kitame, et al, in the *Journal of Antibiotics,* Vol. 27, 884–888 (1974) and Vol. 29, 759–761 (1976). Culture conditions, media composition, separation and isolation techniques are given in these two references along with laidlomycin's physical properties.

Esters of laidlomycin also show propionate-enhancing activity. Such esters may be prepared by methods set out in U.S. patent application Ser. No. 162,473, filed June 24, 1980 which is incorporated herein by reference. Esters are readily prepared by reacting laidlomycin or an alkaline metal salt thereof at low temperatures, such as about 0° to 30° C., with a suitable derivative of an alkanoic acid such as a suitable acid halide, e.g. an acid chloride, or an anhydride, for example, acetyl chloride, propionyl chloride, butyryl chloride, valeryl chloride, hexanoyl chloride, or the anhydrides corresponding to the above acid chlorides, and the like.

The reaction is carried out in a suitable inert solvent, preferably a cyclic amine such as pyridine. Generally the reaction is finished in less that 10 hours, 3 hours being needed at 5° C. for the formation of the butyrate. It is preferred to employ between 1 and 2 moles of acid halide per mole of laidlomycin, or to employ between 1 and 2 moles of acid hydride per mole of laidlomycin. Aliphatic and alicyclic acylated laidlomycin compounds wherein the aliphatic or alicyclic moiety contain 2–18 carbons are esters demonstrating propionate-enhancing activity. However it is preferred to employ aliphatic acyl compounds of 2–6 carbon atoms in the practice of this invention.

Laidlomycin butyrate is prepared as follows. Crude laidlomycin (4.8 g) is chromatographed on silica gel using ethyl acetate as the eluant. Eluting with 1 liter of ethyl acetate and collecting the 400–700 ml fractions affords a solution of sodium laidlomycin in ethyl acetate. Removing the ethyl acetate under vacuum gives sodium laidlomycin (2.2 g) having a melting point of 259°–261° C.

A solution of 150 mg of sodium laidlomycin in 5 ml of pyridine is cooled to 5° C. and 100 mg of butyryl chloride is added. After 3 hours at 5° C., the mixture is taken into 25 ml of methylene chloride, washed with 25 ml of hydrochloric acid and 25 ml of brine, then dried over sodium sulfate. The methylene chloride solvent is removed under vacuum and the residue is chromatographed on silica gel using ethyl acetate. Eluting with 1 liter of ethyl acetate and collecting the 50–100 ml fraction gives 130 mgs of the monobutyrate of laidlomycin m.p. 77°–80° C.

By following in principle the above procedure, but substituting other appropriate acid chlorides such as acetyl chloride, pentanoyl chloride, hexanoyl chloride, the monoesters of laidlomycin are prepared.

A further polyether ionophore of the monensin type is one designated antibiotic A204. It is described in U.S. Pat. No. 3,705,238. The identifier A204 is used to include several factors obtained by fermentation form the A204 generating organism. This organism is *Streptomyces albus* and is on unrestricted deposit as NRRL 3384 at the Northern Utilization Research and Development Div., Agricultural Research Service, U.S. Department of Agriculture, 1815 North University Street, Peoria, Ill. 61604. Details of the fermentation process are given in the above stated patent.

A204 is comprised of two main fractions, Factors I and II. Factor I is the most abundant and important. Factor II comprises about 5% of the A204 mixture produced. Several other factors are produced in minor amounts but their exact amounts and activity are as yet undetermined. The structure of the acid form of A204 I can be found in U.S. Pat. No. 3,937,836.

Compound X206 is another unnamed monensin-type polyether ionophore of interest in this invention. This compound was first reported in 1951 by Berger et al, in *J. Am. Chem. Soc.* 73, 295–98 (1951). The Streptomyces organism from which it can be grown is available from the International Center of Information on Antibiotics, c/o 1 Delcambe. 32, Bd. de la Constitution, Liege, Belgium, which lists the organism on page 31 of its Bulletin No. 3 (1966). An example of culture conditions, time to harvest and isolation procedures for X206 are given in U.S. Pat. No. 3,937,836. Structural characterization was carried out by Blount et al, *Chemical Communications* (1971) 927–928.

A further example of a polycyclic ether ionophore which may be used in the practice of this invention is the antibiotic A201 (A201A and A201B) which are produced as fermentation products of an organism which is a strain of *Streptomyces capreolus Higgens,* which organism is on unrestricted deposit under the identifying number NRRL 3817, at the Northern Utilization Research and Development Laboratory, Agricultural Research Service, U.S. Department of Agriculture, Peoria, Ill. Examples of nutrient media, growing conditions and harvesting techniques are set out in U.S. Pat. No. 3,790,667.

Two polycyclic ether antibiotics of the monensin type, designated as antibiotic compounds 47,433, and 47,434 or mixtures thereof are described in U.S. Pat. No. 4,148,882. These as yet structurally unidentified antibiotics are acidic polycyclic ethers produced by a new species of *Actinomadura macer* Huang sp. Nov. ATCC 31286 under submerged aerobic conditions in aqueous nutrient media. Culture methods, separation and isolation techniques and spectral characterization of these two compounds is set out in the above mentioned patent.

Another compound exhibiting propionate-enhancing properties and classified as a polyether ionophore antibiotic, although its structure is distinct in several aspects from that of monensin, is a compound designated X-14547. It is the fermentation product of a strain of *Streptomyces antibioticus* designated X-14547. A culture of the representative strain has been deposited in the U.S. Department of Agriculture, Agriculture Research Service, NRRL, Peoria, Ill. and added to its permanent collection of microrganisms as NRRL 8167. Methods for growing said bacterium, media separation and isolation of X-14547, and a semi-structural formula can be found in U.S. Pat. No. 4,100,171.

In the same vein as X-14547 is the drug lasalocid, also known by the number X537A. Lasalocid, another product of fermentation, is produced by an organism which is on deposit at the International Center of Information on Antibiotics c/o 1 Delcambe. 32, Bd. de la Constitution, Liege, Belgium. The organism is listed on page 31 of the Center's *Bulletin* No. 3 (1966). Suitable production media, maximized production times, temperatures, medium pH's and recovery techniques for this antibiotic are set out specifically in U.S. Pat. No. 3,937,836. This drug was first disclosed and structurally characterized in Netherland's Patent No. 70.12,180.

Additional compounds of interest are ionomycin and lonomycin. Ionomycin is disclosed in U.S. Pat. No. 3,873,693 to Meyers, et al. This antibiotic is obtained by cultivating the microrganism *Streptomyces conglobatus,* ATCC 31005, in an aqueous nutrient media comprising an assimilable carbohydrate and an assimilable nitrogen source under submerged aerobic conditions until substantial antibiotic activity is imparted to the medium. A culture of the living organism has been deposited and made a part of the stock culture collection of American Type Culture Collection (Rockville, Md.) available under the accession number ATCC 31005.

Lonomycin is produced by the strain TM-481 which is identified as *Streptomyces ribosidificus.* The antibiotic obtained as a sodium salt is a colorless prism having a molecular formula of $C_{44}H_{75}O_{14}Na$ (m.w. 850) m.p. 188°–199° C. Fermentation, isolation and characterization of the antibiotic are described in the *J. Antibiotics,* V. 29, No. 1, p. 15–20 (1976) by S. Omura, et al.

The polyether ionophores most preferred for the practice of this invention are monensin, lasalcoid, salinomycin, dianemycin, narasin nigericin, septamycin, laidlomycin, and laidlomycin esters.

Another group of compounds demonstrating propionate-enhancing activity in ruminants are certain of the peptides antibiotics and their physiologically active salts and complexes.

Of the numerous peptides antibiotics known and which have propionate-enhancing activity, one is of particular interest in the practice of this invention. That antibiotic is designated as AV290 and is produced under controlled conditions by a strain of *Streptomyces candidus.* A viable culture of this strain has been deposited with the Culture Collection Laboratory, Northern Utilization Research and Development Division, U.S. Department of Agriculture, Peoria, Ill. and has been added to its permanent collection as NRRL 3218. The preparation and properties of this antibiotic are set forth in U.S. Pat. No. 3,338,786 which is hereby incorporated by reference. An improved process for the isolation of AV290 is set out in U.S. Pat. No. 3,856,937. This compound is available commercially under the trademark Avoparcin ® from Lederle Laboratories, Wayne, N.J.

In addition to these two general groups of propionate increasing compounds there are a number of other antibiotic compounds which show propionate-enhancing activity in the rumen. Examples of several such compounds are vancomycin, ristocetin, A477 and A-4696. Production and characterization of all four can be found in U.S. Pat. No. 3,816,618.

There may also may be used such compounds as the sulfur-containing peptide class of antibiotics, for example, thiostrepton, siomycin, thiopeptin, sporangiomycin, sulfamcin or taitomycin and their physiologically acceptable salts and complexes. See Muir, L. A., and A. Barretto, Jr., J. Animal Sci., 48:468, 1979.

Thiostrepton is a fermentation product of an organism identified as *Streptomyces azureus,* a culture of which is on unrestricted deposit under the identifying number 3705 in the Walksman Collection at the Rutgers Institute of Microbiology, New Brunswick, N.J. The description, preparation, and characteristics of thiostrepton and its salts are taught U.S. Pat. No. 2,982,689 to Donovick et al.

Platt, U.S. Pat. No. 2,982,698 teaches an improvement in the method of preparation of thiostrepton using this organism.

Thiostrepton is weakley basic and forms salts with strong acids such as hydrochloric and sulfuric acid. In addition, thiostrepton forms a complex with calcium chloride. All the salts and the complex hydrolize in water to yield the free base.

Siomycin as a sulfur-containing peptide antibiotic isolated from cultures of *Streptomyces sioyaensis*, as reported by Nishimura et al, *J. Antibiotics*, Ser. A-15, 255–263 (1959) and consists of major (Siomycin A) and two minor (Siomycin B and C) compounds as reported by Ebata et al, *J. Antibiotics*, 22 (8) 364–368 (1969).

A method of producing siomycin from *Streptomyces sioyaensis* is taught by Nishimura, U.S. Pat. No. 3,082,153. A culture of this organism is on unrestricted deposit under the identifying number ATCC 13989 with the American-Type Culture Collection, Rockville, MD.

The process of this invention can best be carried out by co-administering a propionate-enhancing antibiotic compound and choline or choline compound in amounts such that enough choline is absorbed by the animal to affect animal performance parameters. The amount of antibiotic used will be some amount which increases the production of propionic acid and propionates produced in the rumen, a propionate-enhancing amount. Choline will be added to the diet in some amount which demonstrates a positive affect on animal performance parameters, otherwise known as a diet-supplementing amount of choline. The exact amount of drug will depend on its level of activity. Choline supplementation will vary with the weight of the animal and the amount of drug with which it is co-administered.

The process of this invention can be effected by administering to animals with a developed rumen a diet-supplementing amount of choline which is an amount of about 10 to 250 milligrams (mg) of choline per kilogram (kg) of body weight per day, preferably about 20 to 100 mg/kg/day. These figures are given with reference to choline and will not reflect exactly the amounts administered where the compound is some material other than choline itself. In such an instance the exact amounts employed will be based on the compositions' choline content and the total amount employed will be recalculated so as to administer that compound in an amount sufficient to provide an equivalent amount of choline.

The exact effective amount of propionate-enhancing compound will depend upon the particular drug chosen. Examples of several types of propionate-enhancing drugs have been discussed above. The activity of these drugs is variable, with some being effective at much lower concentrations than others. Therefore one wishing to carry out the practice of this invention would first select a particular drug for co-administration with choline and then determine what amounts of that drug would effect a propionate-enhancing response in a ruminant animal and supplement the animal's diet accordingly.

Several ranges can be set out which will encompass, generally, the amount of material which will increase propionate production in the rumen for such drugs. For example, most propionate-enhancing compounds will be effective at some level between 0.02–10 mg/kg/day per animal but most drugs will elicit a propionate-enhancing response in the rumen when administered at a level of 0.05–2.5 mg/kg/day per animal. Specific ranges for selected compounds are set out below. For example, lasalocid is preferably administered in a range of 0.05–5 mg/kg/day per animal, most preferably in an amount of 0.1–2.5 mg/kg/day. Dianemycin, nigericin and monensin demonstrate a propionate-enhancing effect on rumen microflora when administered in amounts between 0.05–2.5 mg/kg/day per animal. Preferably these compounds will be administered in an amount between 0.1–1.5 mg/kg/day per animal. Septamycin, also identified as A 28695A is preferably administered in an amount of 0.02–2 mg/kg/day but preferably in an amount of 0.05–1 mg/kg/day per animal. A preferred dose of naraisn will be 0.02–5 mg/kg/day, preferably 0.05–1.5 mg/kg/day. The esters of laidlomycin are preferably administered in an amount of 0.01–1 mg/kg/day per animal, but preferably in an amount of 0.3–0.8 mg/kg/day.

Peptide-based antibiotics having utility in this invention may be administered in amounts which parallel the ranges described above for the polyether ionophore compounds. For example, the broadest dose range will be between about 0.05–10 mg/kg/day for both peptide and thiopeptide antibiotics. Avoparcin® will preferably be administered in an amount of 0.1–5.0 mg/kg/day.

Feeder cattle on a growing and fattening diet will be fed a diet, according to the invention, containing about 0.357 to about 8.98 kilograms of choline per ton and from about 0.714 to about 357 grams propionate-enhancing compound per ton, dry matter (DM) basis. The concentrations will generally be somewhat higher for heavier animals. The preferred concentrations in feed for complete balanced feeder cattle rations will be about 0.714 to about 3.75 kilograms of choline compound and about 1.79 to about 89 grams of propionate-enhancing compound per ton of ration, DM basis.

Feed premixes, including concentrates and supplements, will be formulated to contain about 1 to 75 percent of the two active ingredients in a ratio of choline or choline compound in an amount sufficient to provide about 1–1250 parts by weight of choline for every part by weight propionate-enhancing compound, preferably 1–250 parts choline or its equivalent for every part antibiotic compound. The remainder of the mix will comprise an edible inorganic or organic carrier.

The term "co-administering" choline or a choline compound with a propionate-enhancing compound is meant to include administering the compounds simultaneously with each other or preadministering one or the other of the compounds. Thus, propionate-enhancing compounds can be administered several hours before choline supplementation and still affect intraruminal degradation of choline to a degree which will make choline supplementation effective as an animal performance enhancing material while still remaining economically effective. Propionate-enhancing compounds can also be administered sometime after dietary choline supplementation so long as that period does not exceed about 1.5–2 hours. In certain instances the propionate-enhancing compound can be administered as a slow-pay-out bolus. In such cases choline or choline compounds may be administered at will as the continued presence and action of the propionate-enhancing compound will have the same affect as if it was being administered simultaneously with choline. However it is most preferred to orally administer choline and a propionate-enhancing compound simultaneously, both from the point of view of effectiveness of the treatment and secondly, as a simple matter of convenience.

While it is most preferred to co-administer choline materials and the subject antibiotic compounds by means of the animal's feed, these materials may be administered orally in various other forms. For example they can be incorporated into tablets, boluses, or capsules, and dosed to the animal. They may also be incorporated into salt blocks and the like.

Choline or choline compounds and the subject antibiotic compounds may be separately added to feeds but the most practical way to administer these two materials is to prepare a composition of these materials, a premix, and mix this formulation into the feed supply. Such a composition may comprise only choline or a choline compound and a propionate-enhancing compound or these active ingredients may be mixed with a carrier or with other drugs, vitamins, minerals, protein concentrates, and similiar feed supplements and a suitable carrier. These compositions may be prepared in dry granular powder form, as pellets, in the form of pastes or may be formulated as liquid feed supplements and the like. Any type of feed may be medicated with such compositions, including common dry feed, liquid feeds, and pelleted feeds.

The methods of formulating supplemental materials into animal feeds are well known. It is necessary only to calculate the amount of each compound which it is desired to administer to each animal, to take into account the amount of feed per day which the animal eats and then mix in the appropriate amount of choline or choline compound and antibiotic.

For commercial use, the choline and propionate-enhancing compound are most readily and conveniently used as a feed additive premix, feed additive concentrate or feed additive supplement in which the active ingredients are distributed uniformly throughout a standard organic or inorganic animal feed carrier in a concentrated form which is conveniently packaged and shipped to the feed mixer. This premix, concentrate or supplement is then in turn mixed uniformly with a normal diet for the animal as desired by the grower or the feed mixer. Examples of carriers for premix compositions are soybean meal, corn oil, ground corn, barley, wheat, mineral mixtures containing, e.g., vermiculite or diatomaceous earth, corn gluten meal, corn distillers solubles, soy flour or other modestly priced edible ingredients.

"Feed additive premix" refers to a composition that must be diluted for safe use in feed additive concentrate, a feed additive supplement or a complete feed. It contains, among other things, one or more additives in high concentrate in a suitable feed base such that up to 100 pounds must be diluted to produce 1 ton of complete feed. A feed additive premix contains additives at levels for which saftey to the animal has not been demonstrated and/or which may result when fed undiluted in residues in the edible products from food producing animals in excess of the safe levels established.

The phrase "feed additive concentrate" refers to a mix intended to be further diluted to produce a complete feed or a feed additive supplement and is throughout the range not suitable for offering as a supplement or for offering free choice without dilution. It contains one or more additives in a suitable feed stuff such that from 100 to 1000 pounds of concentrate must be diluted to produce 1 ton of a complete feed. Such a premix is unsafe if fed free choice or as a supplement because of danger to the health of the animal or because of the production of residues in the edible products from food producing animals in excess of safe levels established.

"Feed additive supplement" refers to a composition for the diet of an animal which contains one or more food additives and is intended to be further diluted and mixed to produce a complete feed; fed undiluted as a supplement to other feeds; or offered free choice with other parts of the rations separately available. Such a premix is intended to be safe for the animal and to not produce unsafe residues in the edible products from food producing animals if fed according to directions.

In the case of feed additive premix, a preselected unit quantity thereof in the range of about 0.5 to about 100 pounds will contain a preselected quantity of choline or choline compound and a propionate-enhancing compound in one of the ranges set out for each above, depending on the animal to be feed and will be suited to mix with the final feed or diet at the rate of one unit quantity of feed. Such an article may contain from about 1 to 75 percent by weight DM basis of the subject compounds in ratios commenserate with the dose ranges set forth herein. A feed additive concentrate will be prepared and administered in a similiar manner as a premix.

Propionate-enhancing compounds and choline materials may also be admixed with a suitable carrier such as an edible feed or feed component in the form of a feed additive supplement. If to be fed free choice or as a supplement, choline and antibiotic are provided according to the anticipated daily consumption of the supplement to provide a daily dose of each of these ingredients in one of the ranges specified.

In addition, choline and the subject antibiotic materials may be incorporated directly into feeds by a mill or other feed supplier to provide a finished feed product to the grower. A finished feed product could be made up of any of the various grains, lucerne, grasses, minerals, vitamins, protein supplements, drugs and the like which go into the formulation of a nutritionally complete ruminant feed. Choline materials and propionate-enhancing compounds may be mixed directly with cattle feed made up of various components such as hay, straw, silage, cornstalks, cottonseed hulls, oats, barley and cereal brans, particularly for the ruminants; natural oils such as animal fat or cattle, fish oils, safflower oil, peanut oil, and cotton seed oil; antioxidants, minerals, vitamins, antibiotics, anthelmintics, and other appropriate medicaments.

Choline or a choline compound plus a propionate-enhancing compound can be incorporated into tablets, drenches, boluses, capsules or premixes. Formulation of these active ingredients into such dosage forms can be accomplished by means of methods well known in the pharmaceutical formulation arts.

Capsules are readily produced by filling gelatin capsules with any desired form of the two active ingredients. If desired these materials can be diluted with an inert powdered diluent, such as sugar, starch, purified crystalline cellulose, or the like to increase the volume for convenience of filling capsules.

Tablets containing choline material and a propionate-enhancing compound can be made by conventional formulation processes. In addition to the active ingredients, tablets may contain a base, a disintegrator, an absorbent, a binder, and a lubricant. Typical bases include lactose, find icing sugar, sodium chloride, starch and mannitol. Starch is also a good disintegrator as is alginic acid. Surface-active agents such as sodium lauryl sulfate and dioctyl sodium sulphosuccinate are also sometimes used. Commonly used absorbents include starch and lactose. Magnesium carbonate is also useful for oily substances. As a binder there may be used, for example, gelatin, gums, starch, dextrin, polyvinyl pyrrolidone and various cellulose derivatives. Among the commonly used lubricants are magnesium stearate, talc, paraffin wax, various metallic soaps, and polyethylene glycol.

Drenches are prepared most readily by choosing a water-soluble form of a propionate-enhancing compound and choline or choline salt. A water-soluble form of one ingredient may be used in conjunction with a water-insoluble form of the other by preparing a suspension of one with an aqueous solution of the other. Water-insoluble forms of either active ingredient may be prepared as a suspension or in some physiologically acceptable solvent such as polyethylene glycol.

Suspensions of water-insoluble forms of either active ingredient can be prepared in oils such as peanut, corn, sesame oil or the like; in a glycol such as propylene glycol or a polyethylene glycol; or in water depending on the solubility of a particular active ingredient.

Suitable physiologically acceptable adjuvants may necessary in order to keep the active ingredients suspended. The adjuvants can be chosen from among the thickeners, such as carboxymethylcellulose, polyvinyl pyrrolidone, gelatin and the alginates. Surfactants generally will serve to suspend the active ingredients, particularly the fat-soluble propionate-enhancing compounds. Most useful for making suspensions in liquid nonsolvents are alkylphenol polyethylene oxide adducts, naphthalenesulfonates, alkylbenzene-sulfonates, and the polyoxyethylene sorbitan esters.

In addition many substances which effect the hydrophilicity, density and surface tension of the liquid can assist in making suspensions in individual cases. For example, silicone anti-foams, glycols, sorbitol, and sugars can be useful suspending agents.

Additionally the subject compounds of this invention may be separately administered, for example, by adding one directly to feed stuffs and co-administering the second material as a bolous tablet, drench, or capsule. Or each may be separately prepared and separately added to feed stuffs in appropriate quantities and at appropriate times. For example, such a material as choline stearate, a fatty acid complex which may be used in the practice of this invention, may not be appropriate for incorporation into feed premixes because of its physical characteristics. In such an instance the choline stearate composition could be provided separately in a suitable diluent such as, for example, corn flour, ground corn cob, hominy, corn glutenmeal, wheat middlings, soybean meal, soybean mill feed, rice mill by-product, and the like and mixtures thereof.

While it is most preferred to carry out the methods of this invention by oral co-administration of the described materials, similar results could be obtained by parenteral administration of solution and suspensions of either or both materials, for example, by intraruminal injection.

The invention is further illustrated by the following non-limiting examples illustrating the various choline material/propionate-enhancing compound formulations which may be used in the practice of this invention.

EXAMPLE 1

| Ingredient | Weight Percent (D.M. Basis) |
|---|---|
| Mixed Hay | 40.0 |
| Ground Yellow Corn | 44.0 |
| Soybean Oil Meal | 7.0 |
| Cane Molasses | 7.0 |
| Dicalcium Phosphate | 0.5 |
| Trace Mineral Salt | 0.5 |
| Vitamin A | 300 IU/lb |
| Vitamin D | 150 IU/lb |
| Choline chloride | 0.04-0.99 |
| Monensin | 0.714 to 357 grams/ton of feed |

Such a feed typically contains 8 to about 15 percent by weight moisture.

EXAMPLE 2

| Ingredients | Weight Percent (D.M. Basis) |
|---|---|
| Ground Shelled Corn | 64.86 |
| Mixed Ground Hay | 20.0 |
| Dried Molasses | 6.00 |
| Soybean Meal | 6.00 |
| Choline chloride | 0.04 to 0.99 |
| Monensin | 0.714 to 357 grams/ton of feed |
| Trace Mineral Salt | 0.50 |
| Dicalcium Phosphate | 0.40 |
| Ground Limestone | 0.70 |
| Vitamin A (30,000 units/gms) | 66.7 grams/ton |
| Vitamin $D_2$ (16,000,000 units/lb) | 7.1 grams/ton |

Such a feed typically contains about 8 to about 15 percent by weight moisture.

EXAMPLE 3

For use in the field or for range animals, the monensin and choline chloride combination may be administered by means of salt or molasses blocks. A typical block may be prepared using the following compositions:

| Ingredients | Weight Percent (D.M. Basis) |
|---|---|
| Dried Cane Molasses | 30.2 |
| Ground Soybean Hulls | 29.6 |
| Choline Chloride | 12.6 |
| Monensin | .48 |
| Granulated Salt | 24.0 |
| Trace Minerals and Vitamins | 0.24 |
| Stablized Animal Fat | 1.3 |
| Moisture | 2.6 |

EXAMPLE 4

If desired, monensin and choline chloride together may be administered as a part of a liquid animal feed supplement such as a supplement containing a non-protein nitrogen source such as urea in admixture with molasses and other feed ingredients. Such a liquid supplement may be prepared using the following:

| Ingredients | Weight Percent (D.M. Bais) |
|---|---|
| Molasses | 77.27 |
| Water | 12.35 |
| Phosphoric Acid, 85% | 2.70 |

-continued

| Ingredients | Weight Percent (D.M. Bais) |
|---|---|
| Ammonium Sulfate | 2.00 |
| Trace Minerals | .50 |
| Vitamin A, D > E | .50 |
| Salt | 1.00 |
| Choline Chloride | 2.63 |
| Monensin | .10 |
| | 100.00% |

EXAMPLE 5

An example of a suitable feed additive premix of choline and propionate-enhancing compound is as follows:

| | |
|---|---|
| Rumensin ®-60* | 110g |
| Choline Chloride | 444.5g |
| Ground corn cobs | 444.5g |

*60g of Monensin/lb of product. Available from Eli Lilly > Co. Indianapolis, IN.

This mixture is then added to the final diet at 2.25 kg per ton of feed.

In any of the foregoing tables and discussion propionate-enhancing compounds other than monensin may be used or two or more such compounds may be added on an equal weight or weight percent basis. Choline materials other than choline chloride, as well a mixtures of choline materials may be substituted in place of the choline chloride on an equivalency basis.

What is claimed is:

1. A method for increasing the availability of supplemental dietary choline to an animal with a developed rumen, which method comprises co-administering a diet-supplementing amount of choline or a choline compound with a propionate-enhancing amount of a propionate-enhancing antibiotic compound.

2. The method of claim 1 wherein said compound is a polyether ionophore or a peptide antibiotic compound.

3. The method of claim 2 wherein said animal is a bovine or a sheep.

4. The method of claim 3 wherein said compound is a polyether ionophore co-administered in an amount of 0.02–10 mg/kg/day with an amount of choline or choline compound sufficient to provide 10 to 250 mg of choline per kilogram of body weight per day.

5. The method of claim 4 wherein said compound is monensin, lasalocid, salinomycin, dianemycin, nigericin, septamycin, narasin, laidlomycin or a laidlomycin ester.

6. The method of claim 5 wherein 0.05–2.5 mg/kg/day of monensin is co-administered with an amount of choline or a choline compound sufficient to provide 20–100 mg/kg/day of choline.

7. The method of claim 5 wherein 0.05–1.5 mg/kg/day of narasin is co-administered with an amount of choline or a choline compound sufficient to provide 20–100 mg/kg/day of choline.

8. The method of claim 5 wherein 0.1 to 1.0 mg/kg/body weight of a laidlomycin ester is co-administered with an amount of choline or choline compound sufficient to provide 20–100 mg/kg/day of choline.

9. The method of claim 8 wherein 0.1 to 1.0 mg/kg/body weight of laidlomycin butyrate is co-administered with an amount of choline or choline compound sufficient to provide 20–100 mg/kg/day of choline.

10. The method of claim 3 wherein said compound is a peptide antibiotic compound co-administered in an amount of 0.05–10 mg/kg/day with an amount of choline or choline compound sufficient to provide 10–250 mg/kg/day of choline.

11. The method of claim 10 wherein said compound is AV290 or AV290-alkyl sulfate co-administered in an amount of 0.1–5.0 mg/kg/day with an amount of choline or choline compound sufficient to provide 20–100 mg/kg/day of choline.

12. The method of claim 8 wherein 0.1 to 1.0 mg/kg/body weight of laidlomycin propionate is co-administered with an amount of choline or choline compound sufficient to provide 20–100 mg/kg/day of choline.

13. A composition for increasing the availability of supplemental dietary choline to an animal with a developed rumen, which composition comprises a diet-supplementing amount of choline or a choline compound, a propionate-enchancing amount of a propionate-enhancing antibiotic compound and a suitable carrier.

14. The composition of claim 13 which comprises choline or choline compound sufficient to provide 1–1250 parts by weight of choline for every part by weight of propionate-enhancing compound and wherein the active ingredients are present in an amount of 1 to 75 percent and the balance is an edible organic or inorganic carrier.

15. The composition of claim 14 wherein said compound is a polyether ionophore.

16. The composition of claim 15 comprising choline or choline compound sufficient to provide 1 to 250 parts choline for every part polyether ionophore.

17. The composition of claim 16 wherein said compound is a polyether ionophore which is monensin, lasalocid, salinomycin, dianemycin, nigericin, septamycin, narasin, laidlomycin or a laidlomycin ester.

18. The composition of claim 17 wherein said compound is laidlomycin butyrate.

19. The composition of claim 14 wherein said compound is a peptide antibiotic compound.

20. The composition of claim 19 comprising choline or choline compound sufficient to provide 1 to 250 parts choline for every part peptide antibiotic compound.

21. The composition of claim 20 wherein said compound is AV290 or AV290-alkyl sulfate.

22. The composition of claim 17 wherein said compound is laidlomycin propionate.

23. A feed composition for increasing the availability of supplemental dietary choline to a ruminant animal which comprises a diet-supplementing amount of choline or a choline compound, a propionate-enchancing amount of a propionate-enhancing antibiotic compound and cattle feed.

24. The composition of claim 23 wherein said antibiotic is a polyether ionophore present in an amount of 0.714–357 grams/ton of feed and an amount of choline or choline compound sufficient to provide 0.357–8.98 kilograms of choline per ton of feed, dry matter basis.

25. The composition of claim 24 wherein said antibiotic is monensin, lasalocid, salinomycin, dianemycin, nigericin, septamycin, narasin, laidlomycin or a laidlomycin ester.

26. The composition of claim 25 wherein said antibiotic is monensin in an amount of 1.79–89 grams/ton and an amount of choline or a choline compound sufficient to provide 0.714–3.75 kg of choline/ton.

27. The composition of claim 25 wherein said antibiotic is narasin in an amount of 1.79–89 g/ton and an amount of choline or a choline compound sufficient to provide 0.714–3.75 kg of choline/ton.

28. The composition of claim 25 wherein said antibiotic is a laidlomycin ester in an amount of 1.79–89 g/ton and an amount of choline or choline compound sufficient to provide 0.714–3.75 kg of choline/ton.

29. The composition of claim 25 wherein said antibiotic is laidlomycin butyrate in an amount of 1.79–89 g/ton and an amount of choline or choline compound sufficient to provide 0.714–3.75 kg of choline/ton.

30. The composition of claim 23 wherein said compound is a peptide present in an amount of 0.714–357 g/ton and an amount of choline or choline compound sufficient to provide 0.357–8.98 kg of choline/ton.

31. The composition of claim 30 wherein said compound is AV290 or AV290-alkyl sulfate present in an amount of 1.79–89 g/ton and an amount of choline or choline compound sufficient to provide 0.714–3.75 kg of choline/ton.

32. The composition of claim 25 wherein said antibiotic is laidlomycin propionate in an amount of 1.79–89 g/ton and an amount of choline or choline compound sufficient to provide 0.714–3.75 kg of choline per ton.

* * * * *